United States Patent [19]
Ogura

[11] Patent Number: 5,560,365
[45] Date of Patent: Oct. 1, 1996

[54] INFLATABLE CUFF FOR USE IN BLOOD PRESSURE MEASUREMENT

[75] Inventor: Toshihiko Ogura, Inuyama, Japan

[73] Assignee: Colin Corporation, Aichi-ken, Japan

[21] Appl. No.: 347,145

[22] Filed: Nov. 22, 1994

[30] Foreign Application Priority Data

May 19, 1992 [JP] Japan ................................. 4-151566

[51] Int. Cl.$^6$ ................................................. A61B 5/00
[52] U.S. Cl. ..................... 128/680; 606/202; 128/686; 128/682
[58] Field of Search ............................ 128/672, 677–682, 128/685; 606/201, 202

[56] References Cited

U.S. PATENT DOCUMENTS

| | | | |
|---|---|---|---|
| 1,953,466 | 4/1934 | Corwin | 128/677 |
| 3,279,459 | 10/1966 | Schenker | 128/686 |
| 3,669,096 | 6/1972 | Hurwitz | 128/686 |
| 3,906,937 | 9/1975 | Aronson | 128/686 |
| 3,968,788 | 7/1976 | Hopkins | 128/686 |
| 4,832,040 | 5/1989 | Ruff | 128/686 |
| 4,920,971 | 5/1990 | Blessinger | 128/686 |
| 5,433,724 | 7/1995 | Kawasaki et al. | 606/202 |

*Primary Examiner*—Angela D. Sykes
*Assistant Examiner*—Robert L. Nasser, Jr.
*Attorney, Agent, or Firm*—Oliff & Berridge

[57] ABSTRACT

An inflatable cuff for pressing a body portion of a living subject by being wound and inflated around the body portion, in measuring a blood pressure of the subject by detecting a Korotkoff sound produced from an arterial vessel of the body portion pressed by the cuff, at least a portion of the cuff being provided by a stretchable sheet member, so that the cuff is stretchable while being wound and inflated around the body portion of the subject for pressing the body portion of the subject.

3 Claims, 4 Drawing Sheets

INFLATABLE CUFF FOR USE IN BLOOD PRESSURE MEASUREMENT

BACKGROUND OF THE INVENTION

1. Field of the Invention

The present invention relates to an inflatable cuff for use in measuring a blood pressure of a living subject by detecting a Korotkoff sound produced from an artery of the subject.

2. Related Art Statement

There are known two sorts of blood pressure (BP) measuring devices each of a Korotkoff-sound type wherein an inflatable cuff having an elongate, belt-like configuration is wound around, e.g., an upper arm of a living subject such as a patient, and an air is supplied into the cuff to inflate the cuff and thereby press the upper arm, so that systolic and diastolic BP values of the subject are measured by detecting the first and last Korotkoff sounds produced from an artery of the arm while the air pressure of the cuff pressing the arm is slowly decreased. One of the two sorts of BP measuring devices is an automatic BP measuring device including a microphone, and the other is a mercurial manometer used with a stethoscope.

The Korotkoff sound-type BP measuring devices as described above are used for, e.g., measuring BP values of a subject who is undergoing an exercise test. The BP measurement is usually carried out using an automatic BP measuring device including a microphone. The microphone, however, may pick up noise such as frictional sounds of the cuff, so that the signal to noise (S/N) ratio of a Korotkoff-sound signal produced from the microphone may be lowered and accordingly the accuracy of BP measurements based on the Korotkoff-sound signal may be lowered or the BP measurements using the cuff may be made even infeasible. The noise may be removed from the Korotkoff-sound signal, by successively determining an appropriate time window or gate using an R wave of an electrocardiogram (ECG) obtained from the subject as a trigger to start each time gate, and collecting a Korotkoff sound through the thus determined each time gate.

However, even though the noise resulting from the subject's physical motion may be removed from the Korotkoff-sound signal, the accuracy of BP measurements based on the Korotkoff-sound signal may be lowered for other reasons. More specifically, if a certain force is applied to the cuff because of the subject's physical motion during the above-mentioned slow decreasing of the air pressure of the cuff currently pressing the subject' arm, the cuff pressure may considerably largely be changed. Those changes of the cuff pressure adversely influence the detected magnitudes of the Korotkoff sounds that are produced in relation with the state or degree of occlusion of the subject's artery, so that the first and/or last Korotkoff sounds may not be detected by the microphone with accuracy. Consequently the accuracy of BP measurements may be lowered or the BP measurements may be made infeasible. The problem that the changes of cuff pressure due to the subject's motion adversely influence the accurate detection of Korotkoff sounds and eventually the accuracy of BP measurements, will be encountered also in the case where the above-identified mercurial manometer is used with a stethoscope by a doctor or nurse.

A conventional cuff is provided by a cloth substantially incapable of stretching, for preventing an excessive amount of air from being supplied to the cuff. The present inventor has conducted an extensive study for solving the above-explained problem and found for the first time that a cuff capable of stretching advantageously absorbs the changes of cuff pressure due to the subject's physical motion.

SUMMARY OF THE INVENTION

It is therefore an object of the present invention to provide an inflatable cuff which is advantageously used for measuring a blood pressure of a living subject by detecting a Korotkoff sound produced from an artery of the subject, with high accuracy, even with the subject being in physical motion.

The above object has been achieved by the present invention, which provides an inflatable cuff for pressing a body portion of a living subject by being wound and inflated around the body portion, in measuring a blood pressure of the subject by detecting a Korotkoff sound produced from an arterial vessel of the body portion pressed by the cuff, wherein the improvement comprises a stretchable sheet member providing at least a portion of the cuff, so that the cuff is stretchable while being wound and inflated around said body portion of said subject for pressing the body portion of the subject.

In the inflatable cuff constructed as described above, a stretchable sheet member provides at least a portion of the cuff, so that the cuff is stretchable while being wound and inflated around the body portion of the subject for pressing the body portion. While the present cuff including the stretchable sheet member is wound around the subject's body portion and the pressure of the cuff pressing the body portion is slowly changed, blood pressure values of the subject are measured by detecting the first and last Korotkoff sounds produced from the artery of the subject's body portion. Even if forces which can produce considerably great changes in the cuff pressure are applied to the cuff because of physical motion of the subject, those forces are advantageously absorbed by stretching of the stretchable sheet member. Thus, the cuff pressure is free from the problem of being adversely influenced by the forces applied to the cuff. The detection of Korotkoff sounds from the subject's artery is effectively prevented from being influenced by the changes of cuff pressure due to the physical motion of the subject. With the present cuff, the first and last Korotkoff sounds can be detected with high accuracy from the subject even in physical motion. Thus, the accuracy of blood pressure measurements using the present cuff is much improved.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
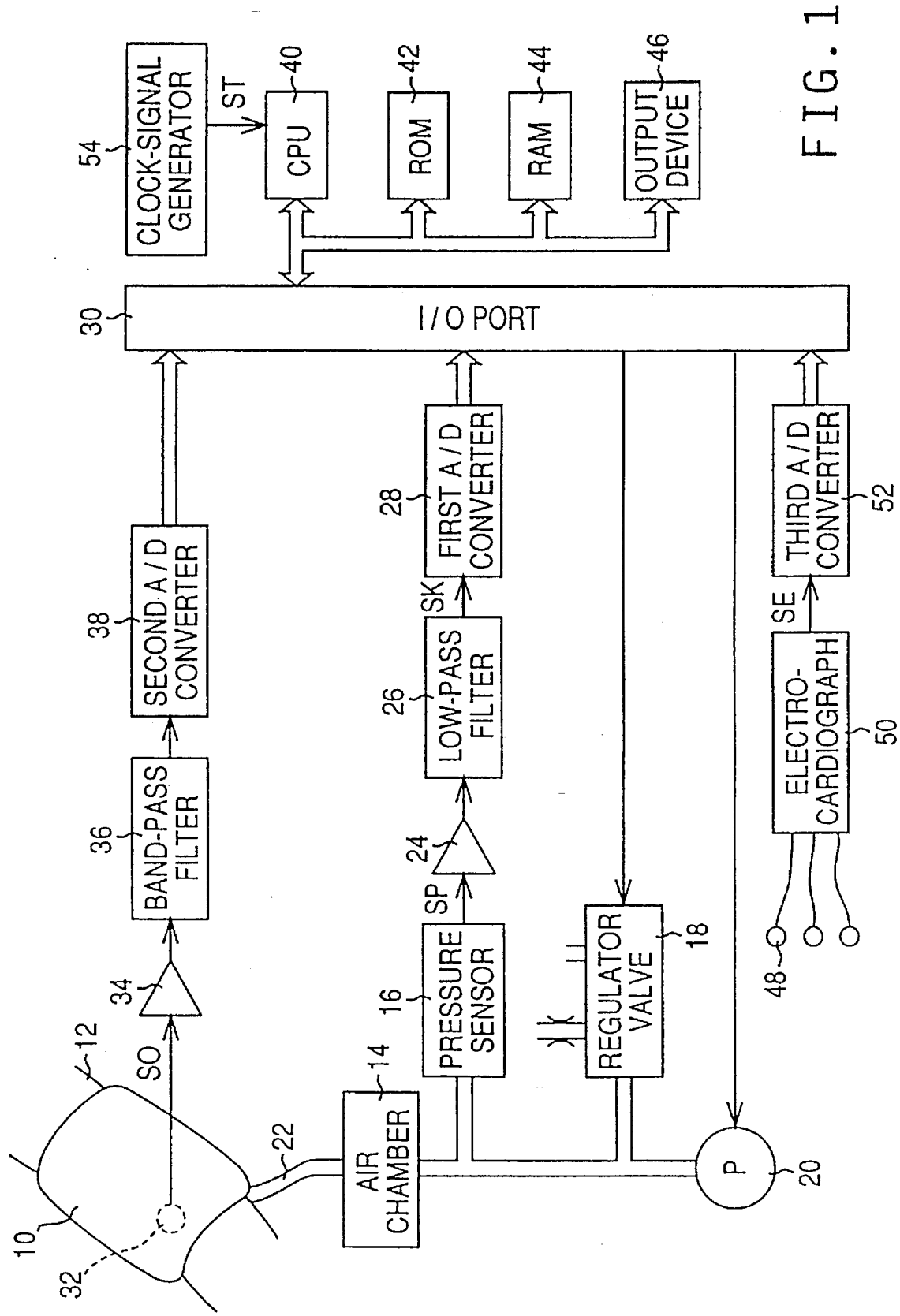
FIG. 1 is a diagrammatic view of an automatic blood pressure (BP) monitor device of a Korotkoff-sound type including an inflatable cuff to which the present invention is applied.

Referring first to FIG. 1, there is shown an automatic blood pressure (BP) monitor including an inflatable cuff 10 to which the present invention is applied. The BP monitor is of a Korotkoff-sound type wherein a BP value of a living subject such as a patient is automatically measured by detecting a Korotkoff sound produced from an artery of the patient being pressed by the cuff 10, as described in detail later. The BP monitor is used for automatically measuring BP values of, e.g., a patient who is undergoing an exercise test such as running.

As shown in FIG. 1, the cuff 10 is set on the patient by being wound around an upper arm 12 of the patient as a body portion of a living subject. The cuff 10 is connected via a piping 22 to an air chamber 14, a pressure sensor 16, a pressure regulator valve 18, and an air pump 20. A pressurized air is supplied from the air pump 20 to the cuff 10 via the air chamber 14, to inflate the cuff 10 wound around the arm 12 and thereby press the arm 12. The pressure sensor 16 detects an air pressure in the cuff 10, and supplies a detection signal, SP, representing the detected air pressure, to a low-pass filter 26 via a first amplifier 24. The low-pass filter 26 permits only a static-pressure component of the detection signal SP to pass therethrough, thereby supplying a cuff-pressure signal, SK, representing the static pressure in the cuff 10 (hereinafter, referred to as the "cuff pressure P"), to an input and output (I/O) port 30 via a first analog to digital (A/D) converter 28. The pressure regulator valve 18 is selectively placed in (a) a cuff-inflation position in which the regulator valve 18 permits the pressurized air to be supplied from the air pump 20 to the cuff 10; (b) a slow-deflation position in which the regulator valve 18 causes the cuff 10 to slowly be deflated; and (c) a quick-deflation position in which the regulator valve 18 causes the cuff 10 to quickly be deflated.

The cuff 10 supports a microphone 32 which detects a Korotkoff sound, i.e., arterial sound produced from a brachial artery running in the arm 12 being pressed by the cuff 10. The microphone 32 supplies a Korotkoff-sound signal, SO, representing the detected Korotkoff sound, to a band-pass filter 36 via a second amplifier 34. The band-pass filter 36 permits only an about 30 to 80 Hz frequency component of the detection signal SP to pass therethrough, thereby supplying the filtered Korotkoff-sound signal SO to the I/O port 30 via a second A/D converter 38.

The I/O port 30 is connected via data bus lines to a central processing unit (CPU) 40, a read only memory (ROM) 42, a random access memory (RAM) 44, and an output device 46. The CPU 40 processes input signals according to control programs pre-stored in the ROM 42 by utilizing a temporary-storage function of the RAM 44. The CPU 40 regulates the cuff pressure P by controlling the air pump 20 and the pressure regulator valve 18 via respective drive circuits (not shown). In addition, the CPU 40 collects the sound signal SO supplied from the microphone 32 while at the same time slowly decreasing the cuff pressure P after having increased the pressure P up to a predetermined target level, and determines, as a systolic and a diastolic blood pressure (BP) value of the patient, a cuff pressure P at the time of detection of the first Korotkoff sound (i.e., time of appearance of successive Korotkoff sounds) and a cuff pressure P at the time of detection of the last Korotkoff sound (i.e., time of disappearance of the successive Korotkoff sounds). The CPU 40 controls the output device 46 to indicate the determined BP values of the patient on a display (not shown) and record the same on a record sheet (not shown). The CPU 40 repetitively carries out the above-explained BP measurement of the patient at regular intervals of time, and operates the output device 46 to output the measured BP values of the patient in each measurement cycle.

The BP monitor further includes an electrocardiograph (ECG) 50 including a plurality of electrodes 48 which are put on respective appropriate positions of the skin of the patient. The ECG 50 supplies an ECG signal, SE, representing an electrocardiogram (ECG) waveform of the patient obtained through the electrodes 48, to the I/O port 30 via a third A/D converter 52. According to the control programs pre-stored in the ROM 42 and utilizing the temporary-storage function of the RAM 44, the CPU 40 operates the output device 46 to display the ECG waveform represented by the ECG signal SE, on one hand, and determines an appropriate time window or gate synchronized with a heartbeat of the patient, by utilizing an R wave of the ECG waveform as a trigger to start the time gate, on the other hand. The CPU 40 collects the Korotkoff-sound signal SO through the respective time gates determined in synchronism with successive heartbeats of the patient, for removing noise due to the patient's running from the signal SO. The CPU 40 uses the thus collected Korotkoff-sound signal SO for determining the BP values of the patient as described above. A clock-signal generator 54 supplies a clock signal, ST, to the CPU 40.

Figure 2:
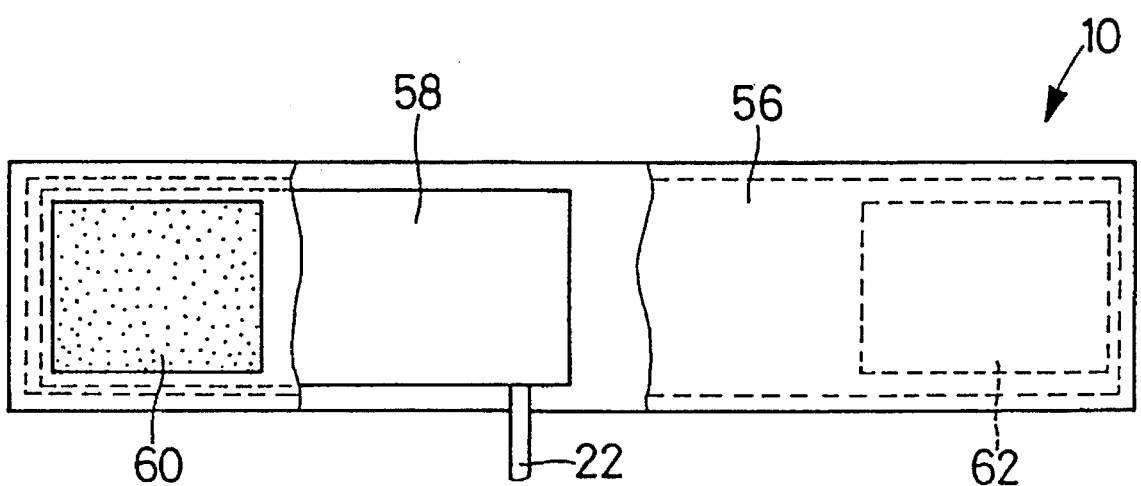
FIG. 2 is a plan view of the cuff of the BP monitor of FIG. 1, the cuff being partly cut away.

As shown in FIG. 2, the inflatable cuff 10 includes a rubber bag 58, and an elongate cloth bag 56 in which the rubber bag 58 is accommodated. A pair of fastener pads 60, 62 are provided on opposite major surfaces of the cloth bag 56 at opposite end portions of the same 56, respectively. With the cuff 10 being wound around the arm 12, the two fastener pads 60, 62 are pressed on each other so that the two fasteners 60, 62 are disengageably held in engagement with each other. Thus, the cuff 10 is fixed around the arm 12. In this situation, the pressurized air is supplied to the rubber bag 58 via the piping 22, so that the arm 12 is pressed by a pressing force corresponding to an air pressure in the rubber bag 58, i.e., cuff pressure P. In FIG. 2, the microphone 32 is not illustrated.

In the present embodiment, the cloth bag 56 is entirely formed of a power stretch fabric. The power stretch fabric may be obtained by weaving about 85% of a nylon-based stretch yarn and about 15% of a polyurethane fiber-based yarn, in an appropriate method and with an appropriate yarn density. The cloth bag 56 is stretchable by about 80% in the longitudinal direction of the cuff 10, and by about 30% in the transverse direction of the same 10. That is, the cloth bag 56 is stretchable up to its maximum elongated length 1.8 time as great as its original length, and up to its maximum elongated width 1.3 time as great as its original width. Even if a force to influence a considerably great change to the air pressure in the rubber bag 58 (i.e., cuff pressure P) is applied to the cuff 10 during the running of the patient, the cloth bag 56 is stretched to absorb the force, thereby avoiding such a pressure change of the rubber bag 58. To this end, the cuff 10 employs the cloth bag 56 as a stretchable sheet member.

Forces to influence considerably great changes to the pressure of the rubber bag 58 may be applied to the cuff 10 during the running of the patient, e.g., (a) in the event that the cuff 10 is partly pinched between the upper arm 12 and its forearm, or the thickness or diameter of the upper arm 12 largely changes while the upper arm 12 and its forearm are repeatedly swung and folded, (b) in the event that the cuff 10 is partly pinched between the arm 12 and the body of the patient while the arm 12 is repeatedly swung, or (c) in the event that the piping 22 whose end portion adjacent to the cuff is not securely fixed to the arm 12 is largely swung or vertically oscillated because of the patient's running. In those events, usually, a pressure oscillation having a low frequency of about 2 to 5 Hz is produced in the air pressure of the rubber bag 58. The low-frequency pressure oscillation is effectively absorbed by the stretching of the cloth bag 56. The pressure change of the rubber bag 58 due to the patient's running is also absorbed to some extent by the air chamber 14 provided between the cuff 10 and the pressure sensor 16.

Figure 4:
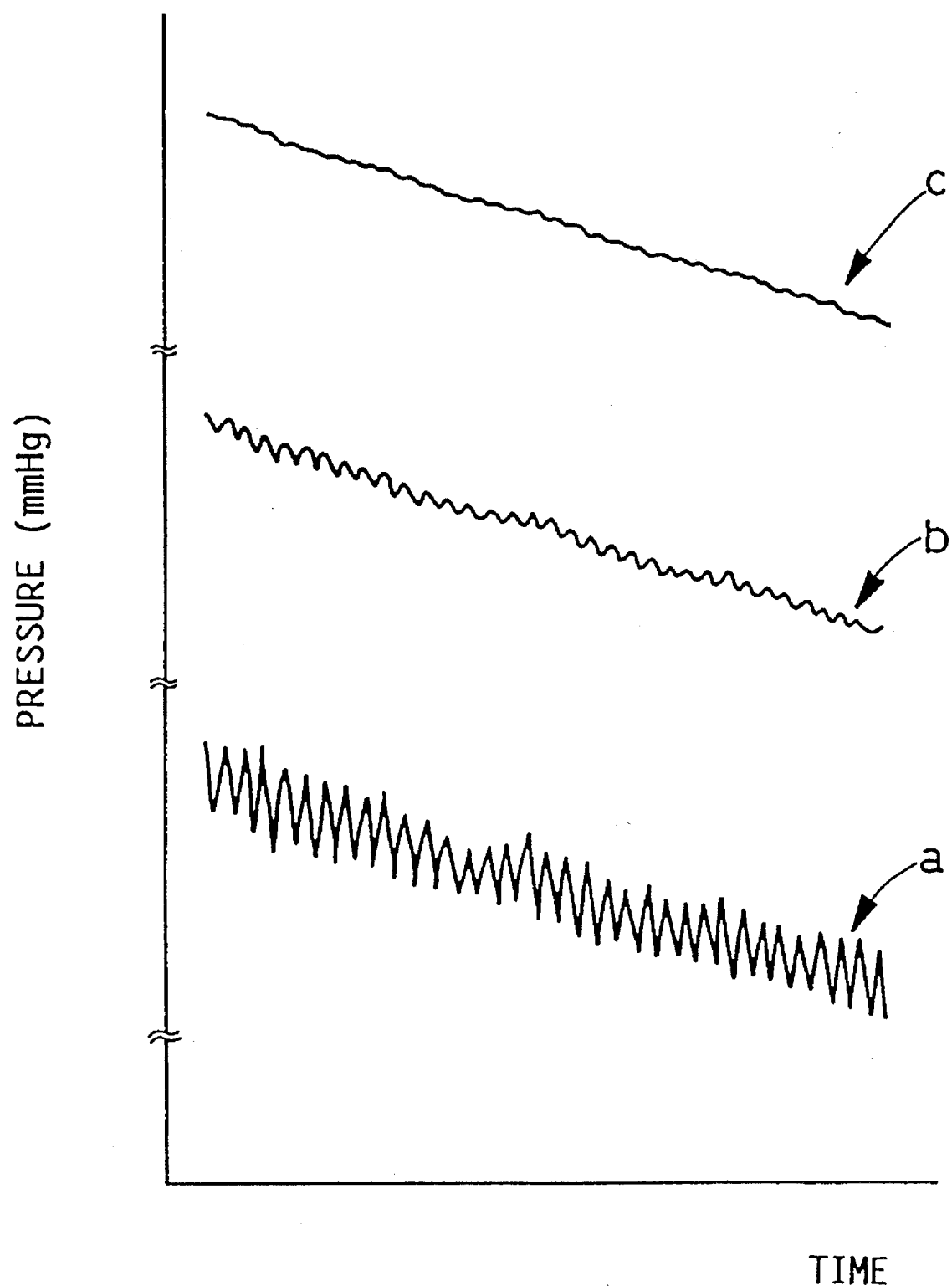
FIG. 4 is a graph corresponding to FIG. 3, showing three curves representing respective pressure changes detected or obtained at three points in the BP monitor of FIG. 1 wherein a conventional cuff is used in place of the invention cuff, while the air pressure of the cuff is slowly decreased in measuring BP values of the subject under the same physical-motion condition as that employed for obtaining the graph of FIG. 3.

FIG. 4 shows three curves, a, b, and c, representing respective air pressure changes detected or obtained at three points in the BP monitor where, however, a conventional inflatable cuff wherein a cloth bag substantially incapable of stretching is employed in place of the cloth bag 56 is used in place of the invention cuff 10, while the air pressure in the conventional cuff being wound around the upper arm 12 of the patient who is swinging and folding the arm 12 just like when actually running, is slowly decreased for measuring a BP value of the patient. The curve a represents the pressure change detected in a rubber bag of the conventional cuff; the curve b represents the pressure change detected in the piping 22 between the air chamber 14 and the air pump 22; and the curve c represents the change of cuff pressure P, i.e., pressure change indicated by the cuff pressure signal SK supplied from the low-pass filter 26. The curve a shows that the air pressure in the rubber bag of the conventional cuff is oscillated with a considerably great amplitude of about 50 mmHg because of the patient's physical motion. Consequently the state or degree of occlusion of the brachial artery of the patient's arm is periodically and largely changed because of the pressure oscillation of the rubber bag. This adversely affects the respective magnitudes of Korotkoff sounds that are produced in relation with the degree of occlusion of the brachial artery. In some cases, the true first and/or last Korotkoff sounds may not be detected by the microphone 32, and the accuracy of BP measurement may be lowered or the BP measurement itself may be made infeasible.

Figure 3:
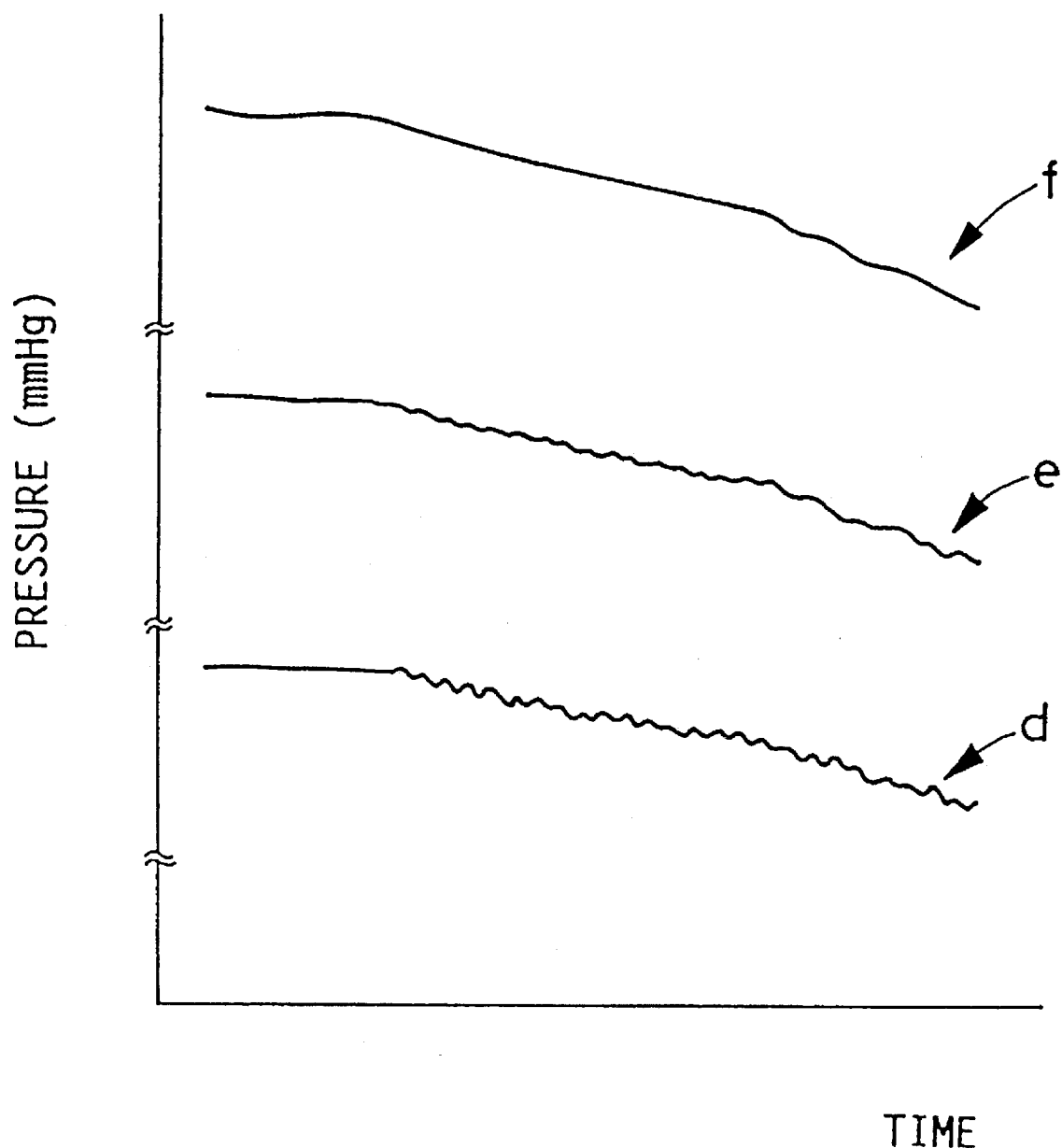
FIG. 3 is a graph showing three curves representing respective pressure changes detected or obtained at three points in the BP monitor of FIG. 1, while the air pressure of the cuff is slowly decreased in measuring BP values of a living subject in physical motion.

In contrast, FIG. 3 shows three curves, d, e, and f, representing respective air pressure changes detected or obtained at the same three points in the BP monitor where the invention cuff 10 is employed, when a BP value of the patient is measured using the same physical-motion condition as that employed in obtaining the curves a, b, c. The curves d, e, f correspond to the curves a, b, c, respectively. The curve d shows that the amplitude of the pressure oscillation produced in the rubber bag 58 of the cuff 10 because of the patient's physical motion is largely reduced as compared with that of the conventional cuff represented by the curve a. Accordingly, the degree of occlusion of the brachial artery of the patient's arm being pressed by the cuff 10 is effectively prevented from being periodically changed because of the pressure oscillation of the rubber bag 58. Thus, the magnitudes of Korotkoff sounds that are produced in relation with the degree of occlusion of the brachial artery, are protected against the periodic change of the degree of occlusion of the brachial artery. Even when the patient is undergoing an exercise test such as running, the true first and last Korotkoff sounds are surely detected by the microphone 32, and the accuracy of BP measurements using the cuff 10 is much improved.

In addition, the curve f shows in comparison with the curve c of FIG. 4 that the pressure signal SK obtained using the cuff 10 is free from an oscillation component resulting from the patient's physical motion. Thus, the BP measurements are effected with improved accuracy based on the values of cuff pressure P when the first and last Korotkoff sounds are detected.

While the present invention has been described in its preferred embodiment, the invention may otherwise be embodied.

For example, while in the illustrated embodiment the cloth bag 56 is entirely formed of a power stretch fabric, it is possible that a power stretch fabric be used to provide only a portion of the cloth bag 56. Such a portion of the cloth bag 56 may be (a) the entire length of an outer half portion of the bag 56 which is adapted to be exposed or visible with the cuff 10 being wound around the arm 12, i.e., adapted not to contact the arm 12; or (b) an intermediate portion of the bag 56 in the longitudinal direction of the cuff. Otherwise, it is possible that at least a portion of the cloth bag 56 be formed of a stretch fabric having a degree of stretch lower than that of the power stretch fabric.

Although in the illustrated embodiment the cloth bag 56 is sufficiently stretchable both in the longitudinal and transverse directions of the cuff 10, it is possible to provide a cloth bag 56 which is sufficiently stretchable only one of the longitudinal and transverse directions of the cuff 10, by employing a stretch fabric obtained using an elastic yarn (e.g., polyurethane yarn) as only one of the warp and woof of the fabric.

While in the illustrated embodiment the cloth bag 56 is formed of a stretch fabric as a stretchable sheet member, it is possible to form a cloth bag 56 of a material other than the stretch fabric, for example, a rubber sheet or a stretchable resin sheet.

Although in the illustrated embodiment the cuff 10 is used with the automatic BP monitor of a Korotkoff-sound type, the cuff 10 may be used with a mercurial manometer and a stethoscope for a stethoscopic BP measurement of a living subject.

While in the illustrated embodiment the air chamber 14 is provided between the cuff 10 and the pressure sensor 16, and the time gates are utilized by the CPU 40, for absorbing pressure changes in the cuff pressure signal SK or removing noise from the Korotkoff sound signal SO, respectively, one or both of those features may be omitted without affecting the advantages of the present invention.

It goes without saying that the automatic BP monitor employing the cuff 10 may be used for measuring a BP value of a living subject different from a patient undergoing an exercise test, for example, a patient at rest.

It is to be understood that the present invention may be embodiment with other changes, improvements, and modifications that may occur to those skilled in the art without departing from the scope and spirit of the invention defined in the appended claims.

What is claimed is:

1. An inflatable cuff device for pressing a body portion of a living subject by being wound and inflated around the body portion, in measuring a blood pressure of the subject by detecting a Korotkoff sound produced from an arterial vessel of the body portion pressed by the cuff device, comprising:

an inflatable bag which is inflatable when a fluid is supplied thereto;

a cloth bag having an elongate shape and accommodating said inflatable bag therein, wherein the cloth bag is entirely formed of a stretchable sheet member, said cloth bag being stretchable while being wound and inflated around the body portion of the subject for pressing the body portion of the subject, the microphone detecting said Korotkoff sound produced from said arterial vessel of the body portion being pressed by said inflatable cuff device.

2. An inflatable cuff device according to claim 1, wherein said stretchable sheet member is formed of a material selected form the group consisting of a stretch fabric, a rubber sheet, and a stretchable resin sheet.

3. An inflatable cuff device according to claim 2, wherein said stretchable sheet member is formed of said stretch fabric which is woven by using an elastic yarn as at least one of a warp and a woof of the fabric.

* * * * *